United States Patent [19]

Wang et al.

[11] Patent Number: 5,488,811
[45] Date of Patent: Feb. 6, 1996

[54] ON-LINE AIR FILTER INTEGRITY TESTING APPARATUS

[75] Inventors: Jianjun Wang, Columbus; Douglas D. Osborn, Lewis Center; Billy D. Cornelius, Powell; Douglas A. Harp, Westerville, all of Ohio

[73] Assignee: Abbott Laboratories, Abbott Park, Ill.

[21] Appl. No.: 391,886

[22] Filed: Feb. 21, 1995

[51] Int. Cl.$^6$ ............................. B65B 57/00; B65B 55/00
[52] U.S. Cl. ..................... 53/52; 53/77; 53/425; 53/426; 55/210
[58] Field of Search ....................... 53/52, 77, 507, 53/508, 55, 426, 425; 96/111, 112; 95/8; 55/217, 212, 210

[56] References Cited

U.S. PATENT DOCUMENTS

| | | | |
|---|---|---|---|
| 4,607,252 | 8/1986 | Neri | 53/77 X |
| 4,964,444 | 10/1990 | Hanerus et al. | 53/425 X |
| 4,992,247 | 2/1991 | Foti | 53/425 X |
| 5,007,232 | 4/1991 | Caudill | 53/426 |
| 5,129,212 | 7/1992 | Duffey et al. | 53/426 |
| 5,152,968 | 10/1992 | Foti et al. | 53/425 X |
| 5,178,841 | 1/1993 | Vokins et al. | 53/425 X |

*Primary Examiner*—James F. Coan
*Attorney, Agent, or Firm*—L. R. Drayer

[57] ABSTRACT

A testing apparatus is disclosed which is useful for determining if air filters are providing clean/sterile air within acceptable aseptic processing and/or clean room operation acceptable contamination levels. The advantage of the disclosed testing apparatus is that air filters may be tested "on-line" during a production process as opposed to the traditional testing methods which included removal of the air filter for off-line testing. Less down-time is experienced using the disclosed testing system. A series of valves positioned at the outputs from the air filters, which allow communication with a particle counter, are controlled by a computer which sequentially activates the valves to test the contamination level of the air which passed through an air filter during the production process.

7 Claims, 7 Drawing Sheets

FIG-2

FIG-3
AUTOMATED FILTER INTEGRITY TEST CONTROL LOGIC

ON-LINE AIR FILTER INTEGRITY TESTING APPARATUS

BACKGROUND AND SUMMARY OF THE INVENTION

The present invention relates generally to air filters employed in food, drug and beverage production processes, and more particularly, to an apparatus for testing the integrity of air filters during a production process.

Air filter integrity is critical in many production environments. Air filter testing is normally performed off-line. By waiting to do off-line tests there is a risk of air filter integrity failure during the production process which may result in unnecessary downtime and waste of product. The present invention works while a production process is ongoing and thus the system is referred to as an "on-line" air filter integrity test system. The present invention uses a single test unit and several programmable control valves with customized software to perform predetermined programmable air filter integrity tests while a production system is on-line. The software enables the system to be programmed to stand-by during steam/hydrogen peroxide sterilization by sensing temperature and moisture in the system and to operate on-line after sterilization, to provide an alarm upon sensing a prespecified criteria and to check multiple air filter systems sequentially or individually, either in automatic or manual mode during production, without loss of sterility of the production system.

The most common method of testing air filter integrity is to remove the air filters while the production system is off-line. The entire air filter housing and assembly may be removed from the system and tested. This conventional method suffers from several disadvantages. First, it takes a significant amount of time to manually remove the air filters from the system for testing. Secondly, damage can occur to the air filter apparatus when it is being manually handled. Third, the air filters are sometimes not replaced properly when being re-installed. Fourth, the off-line testing has traditionally been done at predetermined time intervals which can, and does, result in a failure of air filters during the production process which leads to wasted product and more down time.

The present invention is especially useful on aseptic fillers for food, drug, and beverage production systems, but would also work well in non-aseptic environments. The present invention may also be employed with sterile air supply units or systems requiring automatic on-line air filter integrity monitoring and control. Air filter integrity is critical in aseptic processing for continuously supplying sterile air necessary for an aseptic processing system. The present invention significantly reduces the risk of wasted product caused by air filter integrity failure during the production process. The present invention is quick, accurate and reliable in detecting the cleanliness of the filtered air supplied to an aseptic processing system. The present invention is versatile for applications to automate and control aseptic processing units or systems. The present invention offers significant cost savings for multiple air filter system integrity detection or multiple point contamination monitoring. The present invention includes programmable operation logic and flexible control features. It may remain independent of, or be combined with, the main operating control system, and it offers contamination free testing of the processing system.

The present invention comprises a particle counter in connection with a computer which sequentially detects contaminant levels in the air located in outlet lines from respective air filters in a production environment. Sample lines are connected to the outlets of each air filter in the production system and the computer may be programmed to test the output of each air filter sequentially and preferably continuously during a production process. By placing valves in association with each of the air filters, individual air filters may be isolated for testing. If the air which has passed through an air filter is determined to exceed the predetermined allowable contaminant levels, the testing system includes means for indicating that acceptable contaminant levels have been exceeded and the production process should be stopped until the defective air filter has been replaced.

BRIEF DESCRIPTION OF THE DRAWINGS

To acquaint persons skilled in the art with the principles of the invention, a presently preferred embodiment illustrative of the best mode now contemplated for the practice of the invention is described herein making reference to the attached drawings forming a part of the specification and in which drawings.

DETAILED DESCRIPTION OF PREFERRED EMBODIMENTS

Figure 1:
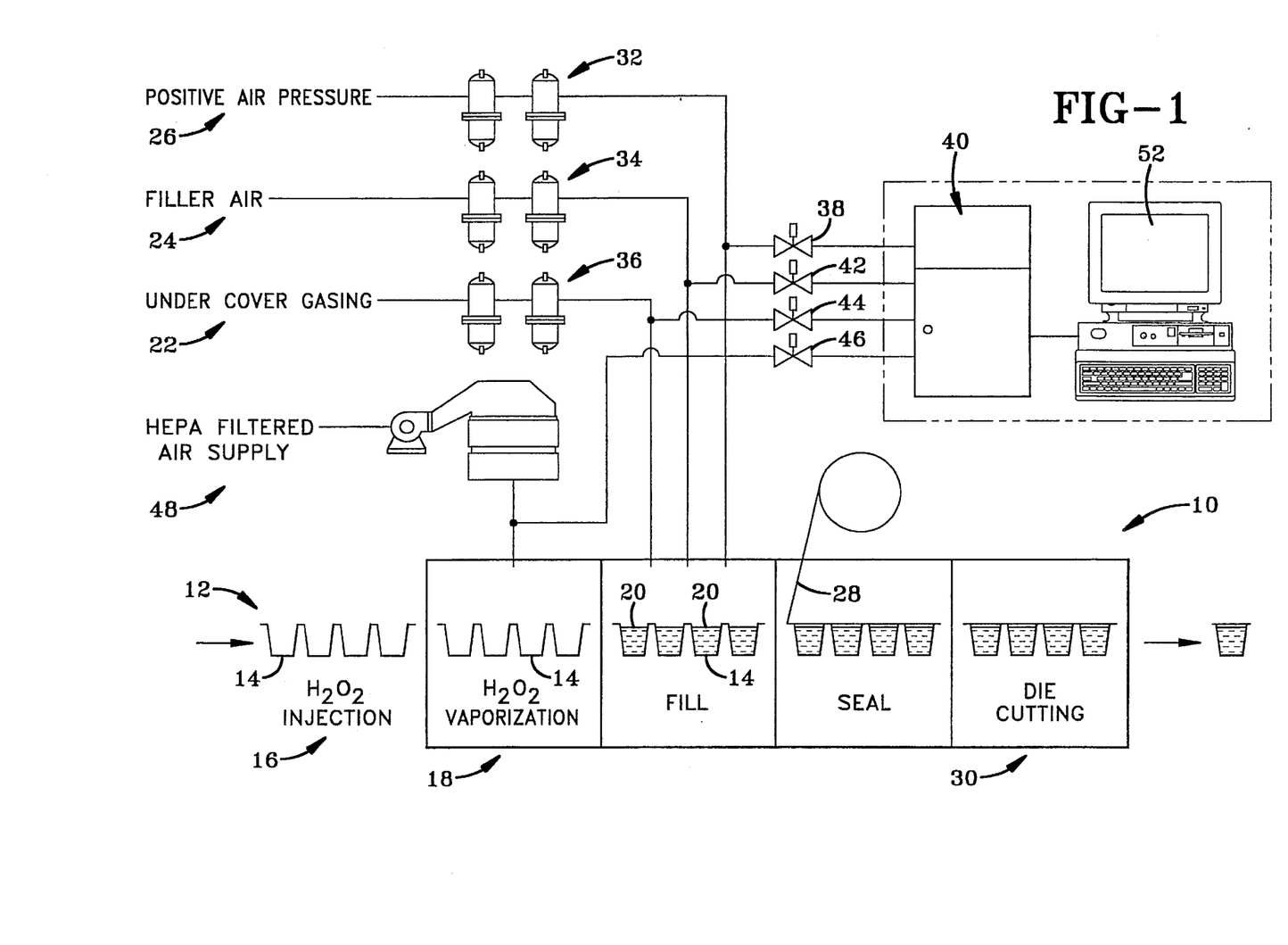
FIG. 1 is a diagrammatic view of a preferred embodiment of the air filter integrity testing apparatus of the present invention.

Referring now to FIG. 1, there is shown a diagrammatic view of an aseptic packaging system 10 employing an apparatus for on-line testing of the integrity of a plurality of air filters. As used herein an "aseptic packaging system" refers to a system in which a sterile product is placed in sterile containers in a sterile zone which are thereafter sealed with a sterile closure, thus eliminating the need for terminal sterilization of a product in a sealed container. As used herein "air" refers not only to the mixture of invisible odorless tasteless gases (such as nitrogen and oxygen) that surrounds the earth, but also to any individual gas such as nitrogen, or other mixture of gasses, that may be employed in a production or packaging process or to provide a desired environment for a production or packaging process. As used herein "air filter integrity" refers to the effectiveness of an air filter in preventing the passage therethrough of particles having a size greater than that which the air filter is intended to remove from air that passes through the filter. As used herein "on-line" refers to the time frame during which a production system is operating to perform its intended function, such as packaging, mixing ingredients, or fabricating a product. As used herein "plurality" is understood to mean two or more.

In this exemplary production process container sheet material 12, such as a polypropylene/EVOH/polypropylene multilayered laminate, is first formed into container shapes 14, such as cups which are interconnected by a web, and then sterilized by a hydrogen peroxide injection 16 into each formed container. Next, the hydrogen peroxide is vaporized 18 by a high efficiency particulate air (HEPA) filtered hot air supply 48. The containers 14 are then filled with a nutritional product 20 preferably in combination with undercover gassing 22, filler air 24, and positive air pressure 26, as known to those of ordinary skill in the art, to maintain the aseptic quality of the filling process just prior to a cover of seal material being applied to each container. In the next step of the production process, the containers 14 are covered and sealed tight with a sheet of seal material 28, preferably of a multilayer, flexible lid stock variety, such as polypropylene/ aluminum foil/polypropylene. The final step 30 in this exemplary aseptic packaging production process is the die cutting of the web of containers into individual containers. An aseptic packaging system requires air that is relatively free of particle contamination and utilizes ultra pure filters (microbial filters) which are designed to prevent passage therethrough of particles equal to or larger than 0.3 µm. If the integrity of such a filter is comprised the product being packaged may have unacceptable levels of contamination and need to be scrapped. Accordingly air filters may be used in series in the hope that redundant filters will not fail simultaneously.

Shown in FIG. 1 are air filters 32 in association with the positive air pressure 26, air filters 34 in association with the filler air 24, and air filters 36 in association with the undercover gassing 22. At a point between the positive air pressure air filters 32 and the containers 14, a valve 38 is positioned and is in communication with: (a) air that has already passed through the air filters 32; and (b) a programmable controller 40. A similar valve 42 is positioned between the filler air filters 34 and the containers 14 and is in communication with: (a) air that has already passed through the air filters 35: and (b) the programmable controller 40. A third valve 44 is positioned between the undercover gassing air filters 36 and the containers 14 and is in communication with: (a) air that has already passed through the air filters 36: and (b) the programmable controller 40. A fourth valve 46 is positioned between the HEPA filter 48 and the container 14 and is in communication with: (a) the programmable controller 40: and (b) air that has already passed through the HEPA filter 48. These valves 38, 42, 44, and 46 facilitate the sampling of air that has already passed through an air filter. A computer 52 communicates with the programmable controller and is employed in the testing apparatus as described below.

Figure 2:
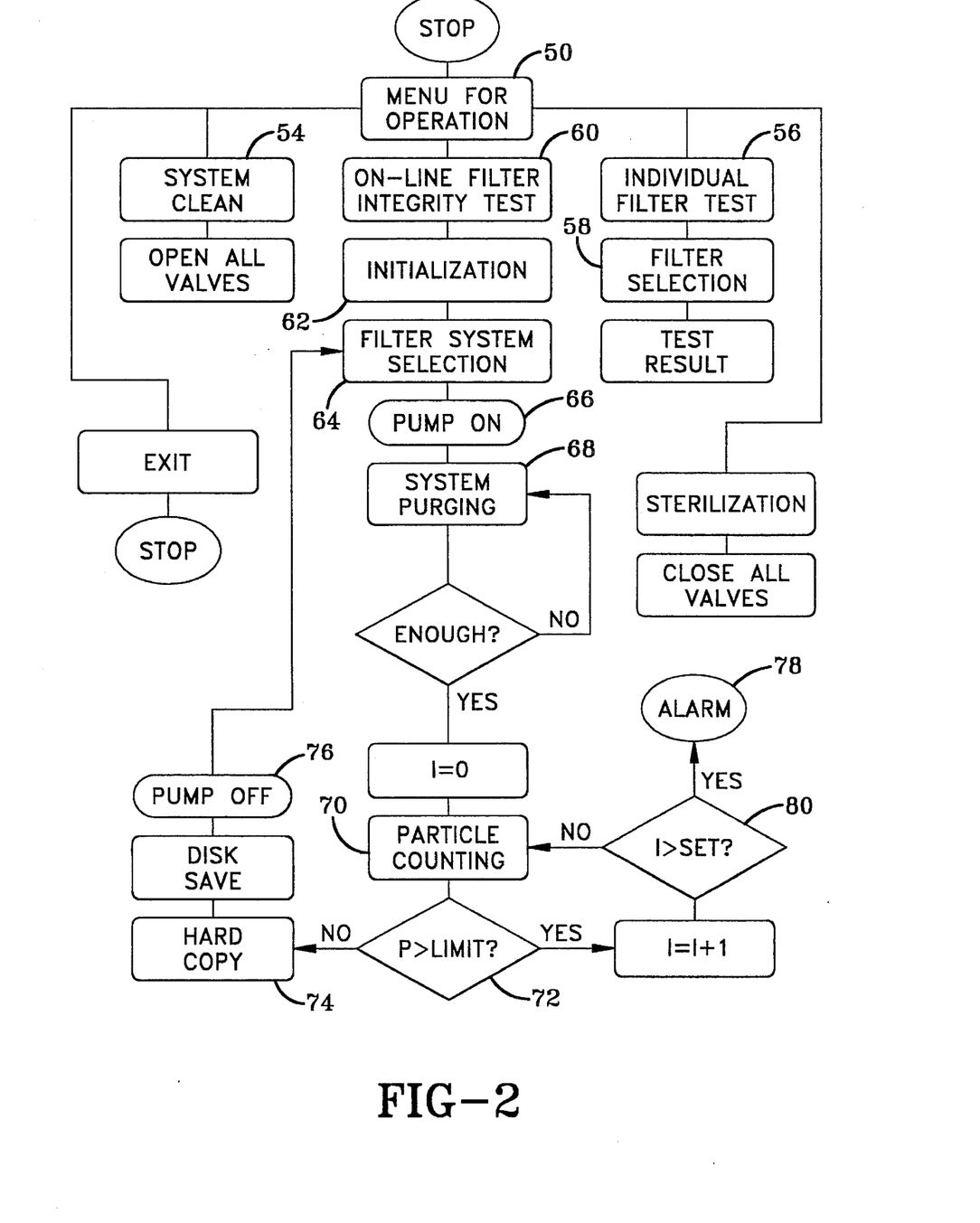
FIG. 2 is a flow diagram of a preferred embodiment of the air filter integrity testing apparatus of the present invention.

Referring now to FIG. 2, a flow diagram of the above described exemplary air filter integrity testing system according to the present invention is shown. An operator may view a menu 50, forming a part of software programmed to run on a computer, to determine the first step of the process. The software code may be written in a number of different ways that would be apparent to one skilled in the art, to operate the air filter integrity testing apparatus as desired by the user. The operator may select to clean 54 the system by opening all valves. The operator may also choose to conduct individual air filter tests 56 through a filter selection menu. Filter integrity is tested using a particle counter known to those of ordinary skill in the art. If the number of contaminant particles having a selected minimum size in air that has already passed through the filter being tested is discovered to exceed a predetermined specific level, then the air filter must be replaced. During steam/hydrogen peroxide sterilization valves 38, 42, 44 and 46 in FIG. 1 are closed to prevent steam/hydrogen peroxide from damaging the particle counter. The residuals of hydrogen peroxide vapor or steam condensate are removed during system clean up 54 before on-line air filter integrity testing.

The operator may also choose to conduct an on-line air filter integrity test 60. After initializing 62 the testing apparatus by preferably inputting maximum acceptable particle numbers and sizes and the sequence and time between tests of different air filters, the computer would then select 64 an air filter(s) to test, activate a vacuum pump 66, and begin system purging 68. The purging would continue until the system has been cleansed sufficiently and a signal is fed back from moisture and temperature sensors attached to the system. Then the first test is initiated by the particle counter 70 determining whether there are more or less particles of contaminated material having a selected minimum size in the air which has already passed through the air filter being tested in relation to a predetermined level 72 of acceptable particle contamination in the air located in output lines from the air filter(s) being tested. As used herein a "predetermined level of acceptable particle contamination" refers to the maximum numbers and sizes of solid particles per unit volume of air that is acceptable in the air supply being tested in a particular production process. If the particle counter determines that there is less particle contamination than the predetermined limit, then a hard copy 74 (that is to say a primed copy) of this result may be obtained, the pump is turned off 76, and the air filter system selection 64 is begun again to test other air filters in the production system. If the particle counter determines that the predetermined level of acceptable particle contamination is exceeded, an alarm 78 may be sounded to stop the on-line production process until the air filter is replaced or verified to be in need of replacement. The particle counter may also be programmed 80 to delay trigger of the alarm until the predetermined level of acceptable particle contamination has been exceeded in more than one sample of air that has already passed through the air filter being tested.

Figure 3:
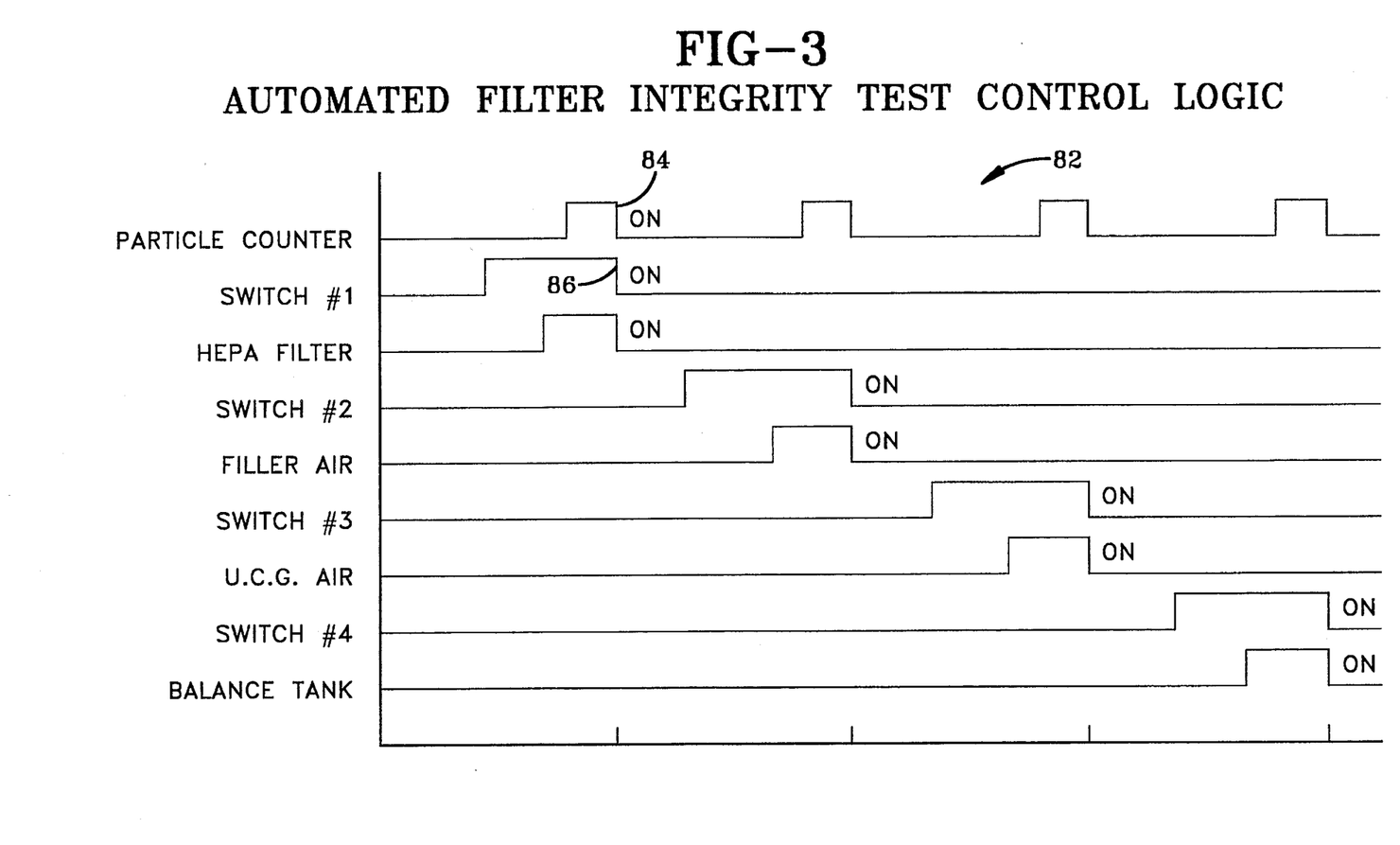
FIG. 3 is a preferred embodiment of the control logic diagram of the present invention.

In FIG. 3, an air filter integrity test apparatus control logic diagram 82 is shown. It can be seen from this diagram that the particle counter is turned on 84 in each instance where a particular air filter is being tested. In order for the particle counter to sense the integrity of the air filter, the valve or switch to the output line containing air which has already passed through that air filter must be open, or on 86, as shown in the control logic diagram.

Figure 4:
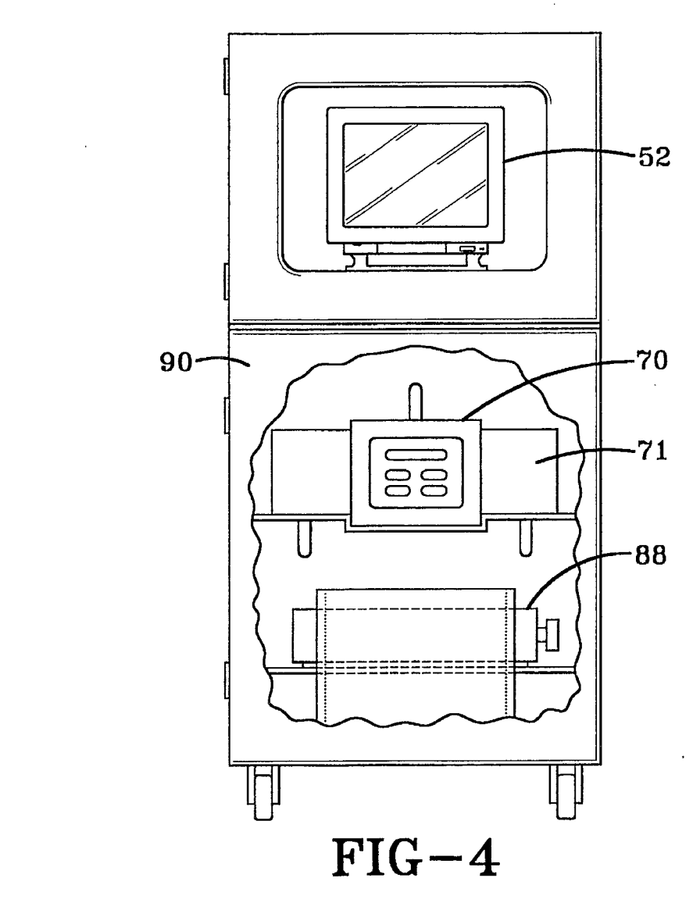
FIG. 4 is an elevational view, partially broken away, of an air filter integrity testing apparatus of the present invention.
Figure 5:
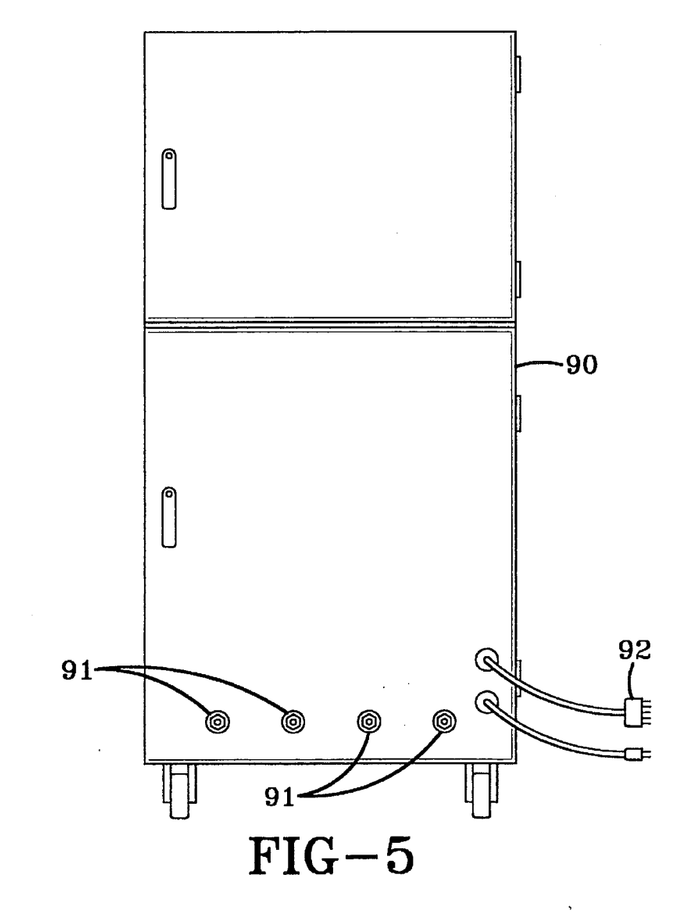
FIG. 5 is a rear elevational view of the apparatus of FIG. 4.

FIG. 4 shows an elevational view, partially broken away, of an exemplary embodiment of an air filter integrity testing apparatus of the present invention in which a computer 52, a particle counter 70 (controlled by the computer ), and a printer 88 are disposed in an enclosure 90 and are arranged to initiate an air filter integrity test, conduct the test, and record the results of the test, respectively. The computer 52, particle counter 70, and printer 88 may all be electronically connected in a conventional manner. FIG. 5 shows the rear of the enclosure 90 housing the various components which may be powered by conventional electric connections. A connector 92 from the computer may be electronically connected to the production process equipment to control and communicate with the production process. For example, the computer may be programmed to stop the production process if the particle counter detects particle contamination that exceeds a predetermined acceptable level in the air which has already passed through an air filter. It is preferable that one set of air filters or an individual air filter be tested at any one time. However, the apparatus of the present invention may be arranged so that multiple air filters are tested at once. If the steam/hydrogen peroxide sterilization procedure is under way, the apparatus will automatically close all valves through the signal feed back from temperature and moisture sensors 71. Particle counters and multiplexed/processors are known to those of skill in the art and a prototype apparatus according to the invention employed a Climet Model C1-4202 0.3 μm particle counter purchased from Climet Instruments Co., Redlands, Calif. Personal computers and printers are commercially available from a number of retail stores. A Gateway 2000, 486DX-33PC with programmable logical controller (the controller), electronically connected to a keyboard for input, was employed in the prototype apparatus. The valves used in the prototype apparatus were electrically actuated by actuator model number 0112 Y6F obtained from Hoke Incorporated of Cresskill, N.J., U.S.A. However, it is understood that any suitable valve actuated by electric, pneumatic or hydraulic means upon receipt of appropriate signals from a controller (e.g. a computer) may be employed in the practice of the invention disclosed herein.

The present invention is applicable to production systems other than the exemplary aseptic packaging system described, which is a preferred embodiment that serves as an example. While aseptic packaging is commonly employed in a food, beverage or drug production packaging process, it is understood that the present invention has utility with regards to any production process which employs filtered air including production processes which are located in a cleanroom where the atmospheric air in a room is filtered by a plurality of air filters.

Figure 6:
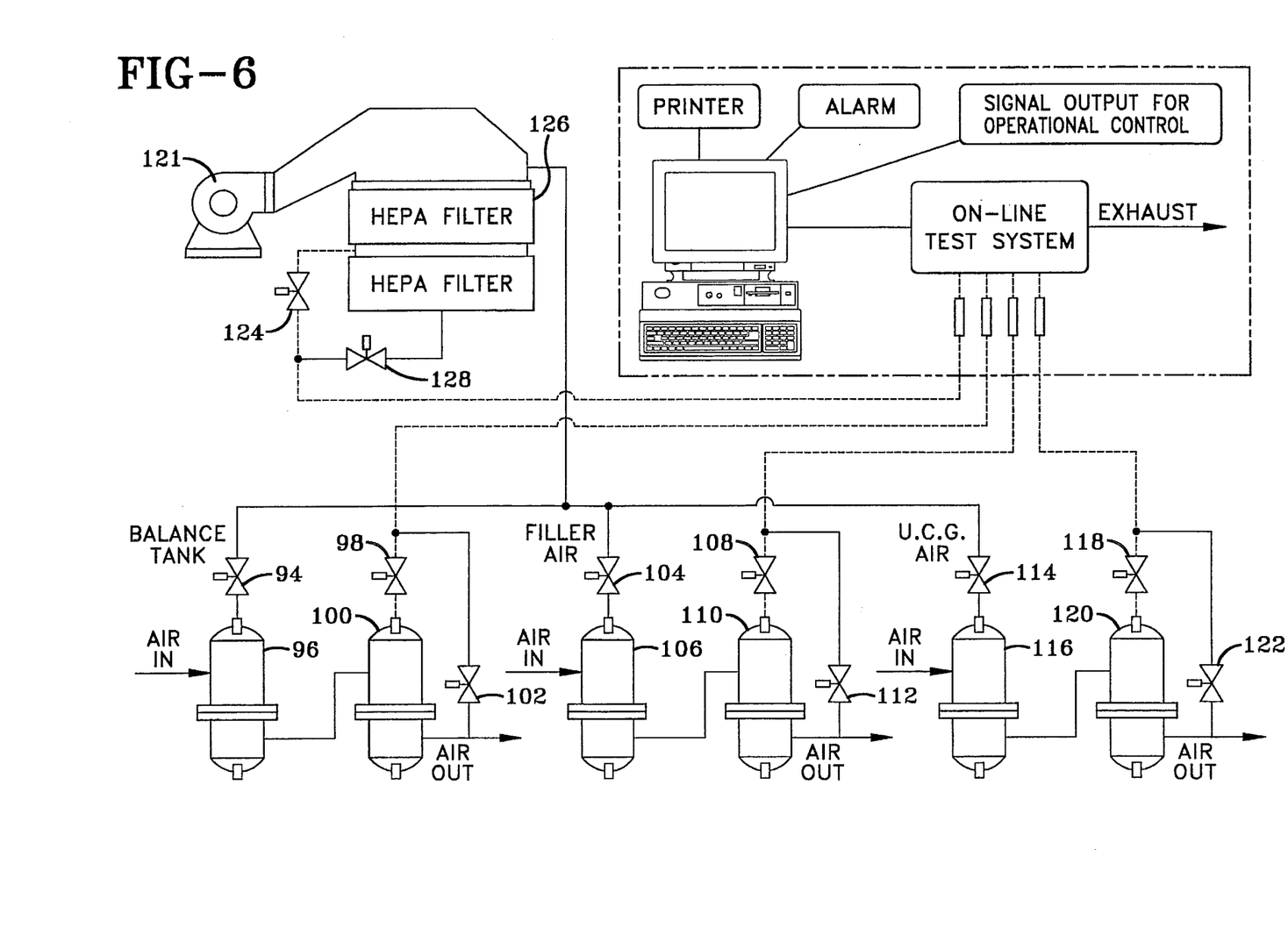
FIG. 6 is a diagrammatic view of another embodiment of the air filter integrity testing apparatus of the present invention.
Figure 7:
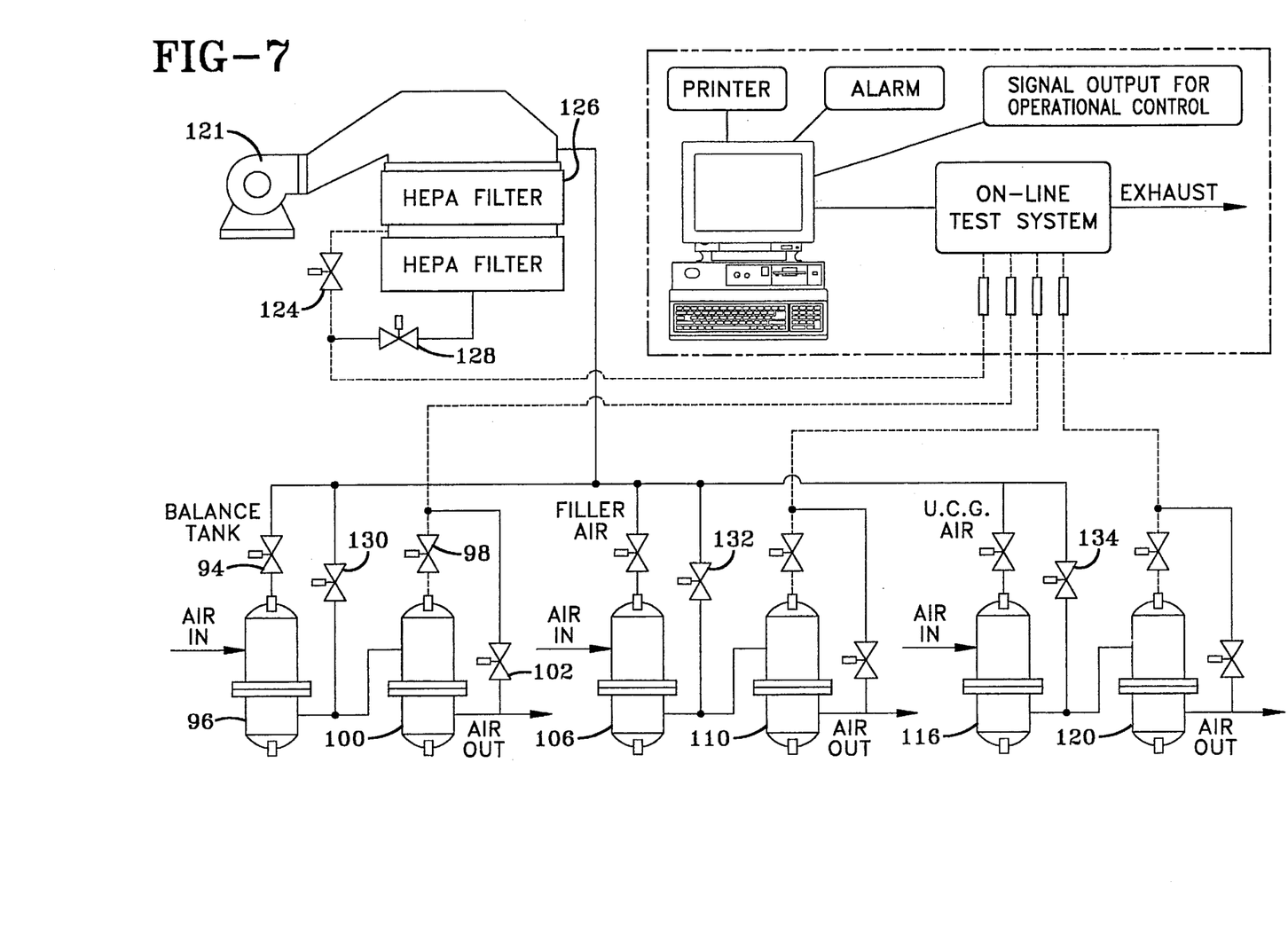
FIG. 7 is a diagrammatic view of yet another embodiment of the air filter integrity apparatus of the present invention.

FIGS. 6 and 7 show two alternative embodiments of air filter integrity test apparatuses of the present invention. In FIG. 6, a first valve 94 is positioned in advance of a first air filter 96 of the balance tank air supply. A second valve 98 is positioned in advance of a second air filter 100 of the balance tank air supply, and a third valve 102 is positioned at the output of the second air filter 100 of the balance tank air supply. A fourth valve 104 is positioned in advance of a first air filter 106 of the filler air supply. A fifth valve 108 is positioned in advance of a second air filter 110 of the filler air supply, and a sixth valve 112 is positioned at the output of the second air filter 110 of the filler air supply. A seventh valve 114 is positioned in advance of a first air filter 116 of the undercover gas (U.C.G.) air supply. An eighth valve 118 is positioned in advance of a second air filter 120 of the undercover gas air supply, and a ninth valve 122 is positioned at the output of the second air filter 120 of the undercover gas air supply. A tenth valve 124 is located in the middle of two HEPA filter systems 126. An eleventh valve 128 is located at the exit of the HEPA filter system 126.

In FIG. 7, an additional valve 130 communicates with the air line connecting the first air filter 96 and second air filter 100 of the balance tank air supply. Another valve 132 communicates with the air line connecting the first air filter 106 and second air filter 110 of the filler air supply. Another valve 134 communicates with the air line connecting the first air filter 116 and the second air filter 120 of the undercover gas (U.C.G.) air supply. In this regard, individual air filters, pairs of air filters and a whole air filter system can be tested individually according to a specific requirement. A complete status about the integrity of the air filters in a production system may be obtained.

With reference to the apparatus shown in FIG. 6, during production, the first, third, fourth, sixth, seventh, ninth and eleventh valves are preferably closed. The second, fifth, eighth, and tenth valves are opened, in turn, according to the initialized sample period of testing for each. For safety, only the first air filters in each air filter system are tested to ensure that there is still a possibility to save the product made up to the point when an air filter failure is detected in an air filter system, if the use of redundant air filters for system integrity can still satisfy the predetermined standard. Such an arrangement also provides an extra protection in case there is a malfunction in any valves. For post-production air filter integrity testing all valves closed during production are now opened by pairs in turn, while all valves open during production are now closed. The preferred operating procedures are as follows: the challenge air from the blower 121 is introduced into the air filter systems through valves 94, 104, 114, and two HEPA filters, flowing through, in turn, from valves 102, 112, 122, and 128 towards the test unit. The air filter system integrity is thus determined.

A method of testing the second air filter in each filter pair separately from testing the first air filter in each pair may be understood with reference to FIG. 7. For example, this may be accomplished by closing the first 94 and second 98 valves while opening the additional valve 130 and third valve 102. This capability is advantageous because air filters employed in production systems may be very expensive. If one air filter in a pair is found to be in need of replacement while the other air filter is still acceptable, only one air filter may have to be replaced, thereby saving the cost of one air filter by not replacing both filters.

Figure 8:
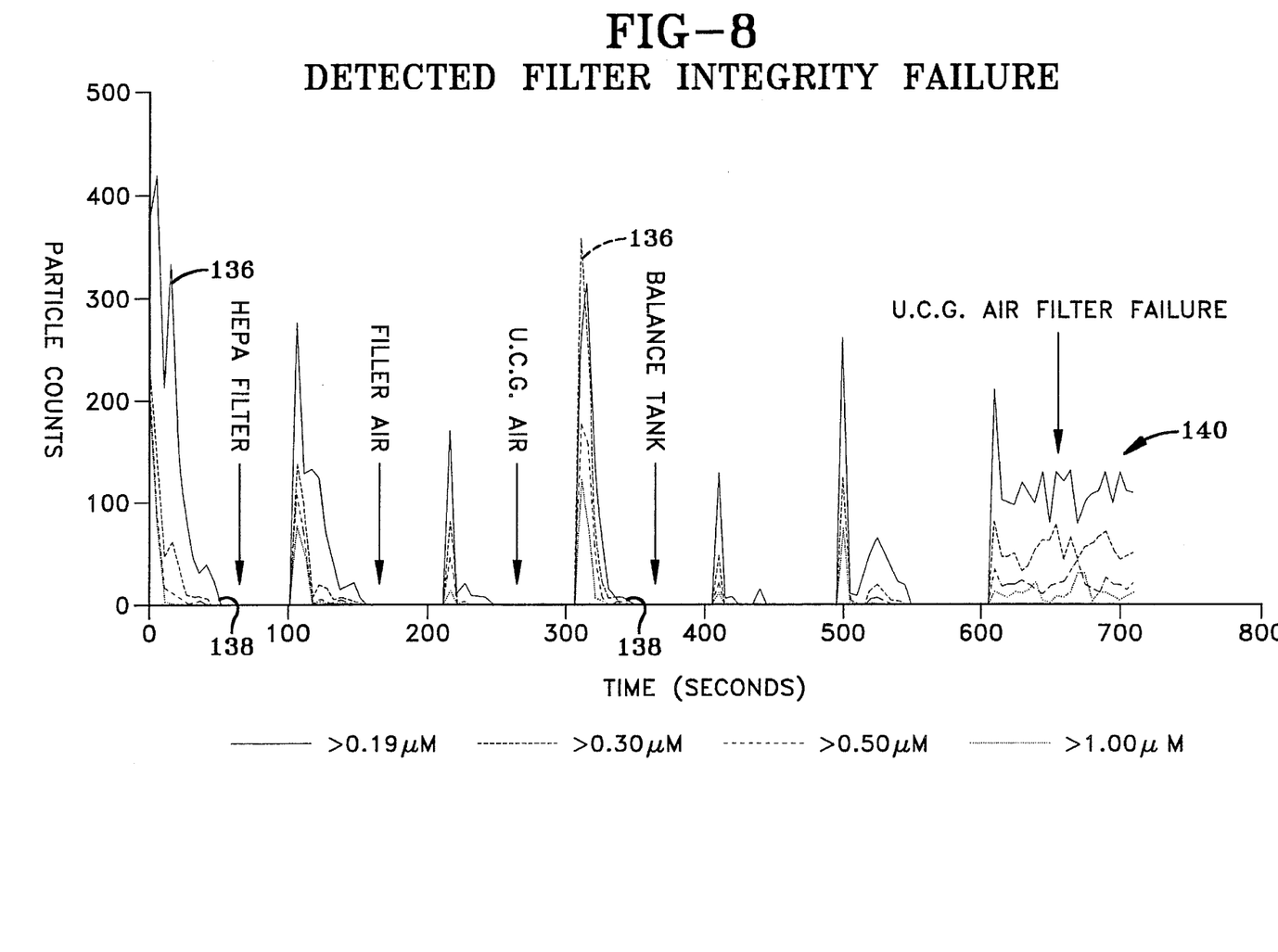
FIG. 8 is a graphical view of a detected air filter integrity failure.

FIG. 8 shows a typical graphical result of various air filter tests. Initially it shows a high particle count 136 as air flow is initiated because of mechanical vibration of the electrical actuators. This is not unusual in the normal operation of air filters. Very quickly, the particle counters will reach a normal operating condition 138. As shown at the far right of the graph, an air filter for the under cover gas has failed as indicated by the high particle count levels 140 shown on the graph. The flow rate is precisely controlled by a flow meter at a predetermined rate.

While the foregoing specification sets forth a detailed description of the preferred embodiment for purposes of illustration, the details herein given may be varied by those skilled in the art without departing from the spirit and scope of the following claims.

We claim:

1. An apparatus for on-line testing of the integrity of a plurality of air filters, said apparatus comprising: a plurality of valves with each valve being connectable for fluid communication with air that has already passed through an air filter in a production system having a plurality of air filters; a programmable controller in communication with each of said valves for sequentially opening and closing said valves upon receiving command information from a system operator; a particle counter in fluid communication with air that has passed through said valves, said particle counter adapted to detect the level of particle contamination in said air, and a computer in association with said programmable controller and said particle counter, said computer adapted to be operated by said system operator to establish (a) a sequence for opening and closing said valves and (b) a predetermined level of acceptable particle contamination present in said air and to activate a warning signal in the event said predetermined level of acceptable particle contamination is exceeded.

2. The apparatus of claim 1, wherein said computer is electronically connectable with a production process controller, such that when said computer determines that an unacceptable level of particle contamination is present in the air that has already passed through an air filter said computer is adapted to command said production controller to halt said production process until said air filter has been replaced.

3. An assembly of an air filter integrity test apparatus assembled with a production system comprising:

(a) a production system which includes a plurality of air filters; and (b) an apparatus for on-line testing of the integrity of a plurality of air filters, apparatus comprising: a plurality of valves with each valve being in fluid communication with air that has already passed through at least one of said air filters; a programmable controller in communication with each of said valves for sequentially opening and closing said valves upon receiving command information from a system operator; a particle counter in fluid communication with air that has passed through said valves, said particle counter adapted to detect the levels of particle contamination in said air, and a computer in association with said programmable controller and said particle counter, said computer adapted to be operated by said system operator to establish (i) a sequence for opening and closing said valves and (ii) a predetermined level of acceptable particle contamination present in said air and to activate a warning signal in the event said predetermined level of acceptable particle contamination is exceeded.

4. The assembly of claim 3, wherein said apparatus for on-line testing of a plurality of air filters further comprises sensors for monitoring temperature and moisture and automatically closes all of said valves in the event moisture and/or temperature readings are beyond predetermined established points.

5. A method for testing the integrity of a plurality of air filters incorporated within a food, beverage, or drug production packaging process, said method comprising the steps of: placing a valve in communication with the air that has already passed through each of said air filters; placing a particle counter in fluid communication with the air which passes through each of said valves; connecting a computer to said particle counter to regulate the sequential testing of each of said air filters by said particle counter, and to indicate when a predetermined acceptable level of particle contamination has been exceeded in the air that has already passed through one of said air filters so that said air filter can be identified and replaced; and, sequentially opening respective valves connected to the respective outputs of each of said air filters, to detect the particle contamination level in the air that has already passed through the air filter being tested.

6. The method of claim 5, wherein said production packaging process is an aseptic production process that incorporates positive air pressure, filler air, and undercover gassing during the filling and sealing portion of the production process.

7. The method of claim 5, further comprising the step of: electronically connecting said computer to a controller of said production packaging process; and, programming said computer to stop said production packaging process in the event that unacceptable levels of particle contamination have been discovered in air which has already passed through any one of said filters.

* * * * *